US012426975B2

(12) United States Patent
Ge et al.

(10) Patent No.: US 12,426,975 B2
(45) Date of Patent: Sep. 30, 2025

(54) INSTRUMENT DRIVE APPARATUS

(71) Applicant: ROBGENIX MEDICAL PTE. LTD., Singapore (SG)

(72) Inventors: Cunwang Ge, Shanghai (CN); Gang Wu, Shanghai (CN); Hao Chen, Shanghai (CN); Xueting Wei, Shanghai (CN)

(73) Assignee: ROBGENIX MEDICAL PTE. LTD., Singapore (SG)

( * ) Notice: Subject to any disclaimer, the term of this patent is extended or adjusted under 35 U.S.C. 154(b) by 0 days.

(21) Appl. No.: 19/068,475

(22) Filed: Mar. 3, 2025

(65) Prior Publication Data

US 2025/0205004 A1    Jun. 26, 2025

Related U.S. Application Data

(63) Continuation of application No. PCT/CN2024/140584, filed on Dec. 19, 2024.

(30) Foreign Application Priority Data

Dec. 20, 2023 (CN) .......................... 202311766806.7

(51) Int. Cl.
*A61B 17/00* (2006.01)
*A61B 34/00* (2016.01)

(52) U.S. Cl.
CPC ........ *A61B 34/71* (2016.02); *A61B 17/00234* (2013.01); *A61B 2017/00327* (2013.01); *A61B 2034/715* (2016.02)

(58) Field of Classification Search
CPC .............. A61B 34/71; A61B 17/00234; A61B 2017/00327; A61B 2034/715; A61B 17/00; A61B 34/30
See application file for complete search history.

(56) References Cited

U.S. PATENT DOCUMENTS

2020/0129255 A1    4/2020  Kallenberger
2022/0233266 A1*   7/2022  Stefan ................... A61B 34/30

FOREIGN PATENT DOCUMENTS

CN    106456256 A    2/2017
CN    107257669 A    10/2017
(Continued)

OTHER PUBLICATIONS

Written Opinion and International Search Report mailed Apr. 2, 2025 in International Application No. PCT/CN2024/140584, with English translation, 15 pages.

*Primary Examiner* — Michael W Kahelin
*Assistant Examiner* — Sebastian X Lukjan
(74) *Attorney, Agent, or Firm* — Nixon & Vanderhye P.C.

(57) ABSTRACT

The present disclosure discloses an instrument drive apparatus comprising an instrument assembly, a first rotating drive assembly, a second rotary drive assembly, and a push-pull drive assembly, the instrument assembly comprising a handle, operating levers slidably connected to the handle, and a rotary rod rotatably connected to the handle; a rotary seat mechanism is connected to the instrument assembly, a first rotary drive mechanism has an output end connected thereto for driving rotation of the instrument assembly; a rotary wheel mechanism is in transmission connection to the rotary rod, a second rotary drive mechanism has an output end connected thereto for driving rotation of the rotary rod; flexible push-pull wires and the operating levers correspond one to one, push-pull drive mechanisms drive reciprocation of the wires to cause the operating levers to reciprocate. The instrument drive apparatus reliably improves the control accuracy and motion stability of the end effectors.

16 Claims, 6 Drawing Sheets

(56) References Cited

FOREIGN PATENT DOCUMENTS

| | | | |
|---|---|---|---|
| CN | 107735044 A | 2/2018 | |
| CN | 112022239 A | 12/2020 | |
| CN | 116269546 A | 6/2023 | |
| CN | 116919482 A | 10/2023 | |
| WO | WO-2015175200 A1 * | 11/2015 | ....... A61B 17/00234 |

* cited by examiner

INSTRUMENT DRIVE APPARATUS

This application is a continuation of International Application No. PCT/CN2024/140584, filed on Dec. 19, 2024, which claims the priority to Chinese Patent Application No. 202311766806.7 filed on Dec. 20, 2023, and entitled "INSTRUMENT DRIVE APPARATUS", the entire disclosure of which is incorporated by reference herein.

TECHNICAL FIELD

The present disclosure relates to the field of medical device technology, and in particular to an instrument drive apparatus.

BACKGROUND

Driven by the continuous technological advancements in medical devices, computer systems, and control mechanisms, minimally invasive surgery (MIS) has been increasingly widely applied due to its advantages such as minimized surgical trauma, expedited recovery and reduced patient discomfort. However, traditional passive MIS instruments when in use require manual operations by surgeons, such as manipulating intermediate transmission mechanisms like sleeves and traction ropes to control distal end effectors for surgical procedures. Such manual operations have limitations, including low control accuracy, susceptibility to misoperations due to hand tremors, and the challenge of mitigating operator fatigue due to prolonged manual operations, which adversely affect the motion control accuracy and stability of the end effectors.

SUMMARY

The present disclosure aims to provide an instrument drive apparatus that addresses the problem that manual operations required in the existing MIS instruments lead to low control accuracy of the end effectors, susceptibility to misoperations due to hand tremors, and operator fatigue, etc., which result in poor motion stability of the end effectors.

To achieve this purpose, the present disclosure adopts the following technical solutions.

An instrument drive apparatus is provided, including:
  an instrument assembly including a handle, at least two operating levers, and a rotary rod, the operating levers being slidably connected to the handle, and the rotary rod being rotatably connected to the handle;
  a first rotary drive assembly including a first rotary drive mechanism and a rotary seat mechanism, the rotary seat mechanism being connected to the instrument assembly, and the first rotary drive mechanism having an output end connected to the rotary seat mechanism;
  a second rotary drive assembly including a second rotary drive mechanism and a rotary wheel mechanism, the rotary wheel mechanism being in transmission connection to the rotary rod, and the second rotary drive mechanism having an output end connected to the rotary wheel mechanism; and
  a push-pull drive assembly including push-pull drive mechanisms and at least two flexible push-pull wires, the flexible push-pull wires being disposed between the operating levers and output ends of the push-pull drive mechanisms respectively.

Optionally, the push-pull drive assembly further includes sliders connected to the operating levers respectively, where each push-pull drive mechanism includes a drive gear, a first transmission rack and a second transmission rack, the first transmission rack and the second transmission rack being meshed with the drive gear at opposite sides and arranged parallel to each other, and each flexible push-pull wire includes a first section and a second section, the first section being connected between the first transmission rack and one end of a corresponding slider, and the second section being connected between the second transmission rack and the other end of the corresponding slider.

Optionally, the push-pull drive assembly further includes sliders connected to the operating levers respectively, and the push-pull drive mechanisms include rotatable drums respectively, the flexible push-pull wires being wound around the drums respectively, with each flexible push-pull wire having a first end connected to one end of a corresponding slider and a second end connected to the other end of the corresponding slider.

Optionally, the push-pull drive assembly further includes a tensioning mechanism including:
  an adjustment bracket and a limit bracket spaced apart from each other and arranged sequentially between the drums and the sliders, the adjustment bracket being provided with a threaded adjustment hole;
  a tensioning sheath disposed between the adjustment bracket and the limit bracket and having one end that abuts against the limit bracket, where a corresponding flexible push-pull wire extends through the tensioning sheath and is slidable with respect thereto; and
  an adjustment bolt threadedly connected to the threaded adjustment hole and abutting against an end of the tensioning sheath that is distal from the limit bracket, so that one end of the tensioning sheath can be pushed by the adjustment bolt to cause the tensioning sheath to bend to tension the flexible push-pull wire.

Optionally, the first rotary drive mechanism includes a rotatable rotary seat driving wheel connected to the rotary seat mechanism, and the second rotary drive mechanism includes a rotatable knob driving wheel connected to the rotary rod, the rotary seat driving wheel and the knob driving wheel being coaxially arranged.

Optionally, the instrument drive apparatus further includes a support tailstock, where the rotary seat driving wheel rotatably extends through the support tailstock and is hollow from one end to the other, and the knob driving wheel extends through the rotary seat driving wheel and is disposed coaxially with respect thereto.

Optionally, the first rotary drive mechanism further includes a first transmission wheel, and the second rotary drive assembly further includes a second transmission wheel, the first transmission wheel and the second transmission wheel being both rotatably connected to the support tailstock and coaxially arranged, where the rotary seat driving wheel is driven by the first transmission wheel to rotate, and the knob driving wheel is driven by the second transmission wheel to rotate.

Optionally, the instrument drive apparatus further includes a linear guide rail extending axially along the handle, with the support tailstock being slidably connected to the linear guide rail; the knob driving wheel is detachably connected to the rotary rod, and the operating lever is detachably connected to the rotary seat mechanism.

Optionally, the first rotary drive mechanism further includes a first drive member and a first transmission gear, the first transmission gear being in transmission connection to the first transmission wheel; and/or the second rotary drive mechanism further includes a second drive member and a second transmission gear, the second transmission gear being in transmission connection to the second transmission wheel.

Optionally, the instrument drive apparatus further includes a linear guide rail extending axially along the handle, with the support tailstock being slidably connected to the linear guide rail; the first rotary drive mechanism further includes a first transmission shaft, and the second rotary drive mechanism further includes a second transmission shaft, the first transmission shaft and the second transmission shaft being both parallel to the linear guide rail, where the first transmission gear is axially slidably mounted on the first transmission shaft, and the second transmission gear is axially slidably mounted on the second transmission shaft.

Optionally, the push-pull drive assembly further includes sliders slidably connected to the rotary seat mechanism including clamping members detachably connected to the operating levers respectively, where the sliders are connected to the clamping members respectively and fixedly connected to the flexible push-pull wires respectively; and/or, the rotary wheel mechanism further includes an inner sheath drive wheel and a knob sleeve, where the inner sheath drive wheel is connected to one end of the rotary rod that is distal from the handle, and the knob sleeve is in transmission connection to the knob driving wheel, the inner sheath drive wheel having external meshing teeth, the knob sleeve having an inner wall provided with internal meshing teeth, with the external meshing teeth and the internal meshing teeth being meshed with each other.

The present disclosure provides an instrument drive apparatus with the following beneficial effects: according to the instrument drive apparatus provided by the present disclosure, the instrument assembly includes a handle, a plurality of operating levers and a rotary rod, the operating levers being slidably connected to the handle, and the rotary rod being rotatably connected to the handle, thus the end effector can be controlled to perform different operations through respective movements of the handle, the operating levers and the rotary rod; the first rotary drive mechanism of the first rotary drive assembly is connected to the rotary seat mechanism to drive the rotation of the instrument assembly, which does not interfere with the push-pull movements of the operating levers and the rotation of the rotary rod, thus multiple operations can be performed either independently or in combination at the same time through the instrument assembly, thereby meeting surgical requirements; the push-pull drive assembly includes multiple flexible push-pull wires in one-to-one correspondence with the multiple operating levers, and the push-pull drive mechanisms that can drive the reciprocation motions of the flexible push-pull wires, which in turn causes the operating levers to reciprocate, where the motions of the driving parts such as motors are converted into the push-pull movements of the operating levers by utilizing the flexibility of the flexible push-pull wires, thereby simplifying the motion transmission chain, which in turn enables the instrument drive apparatus to be lightweight and miniaturized and thus reduces the manufacturing costs. The above-mentioned instrument drive apparatus does not require manual operation, that is, the push-pull movements of the operating levers, the rotation of the rotary rod and the overall rotation of the instrument assembly are all driven by the driving parts, thereby eliminating misoperations due to hand tremors and reducing the operator fatigue associated with the manual operations, thus improving the motion control accuracy of the end effector.

Figure 1:
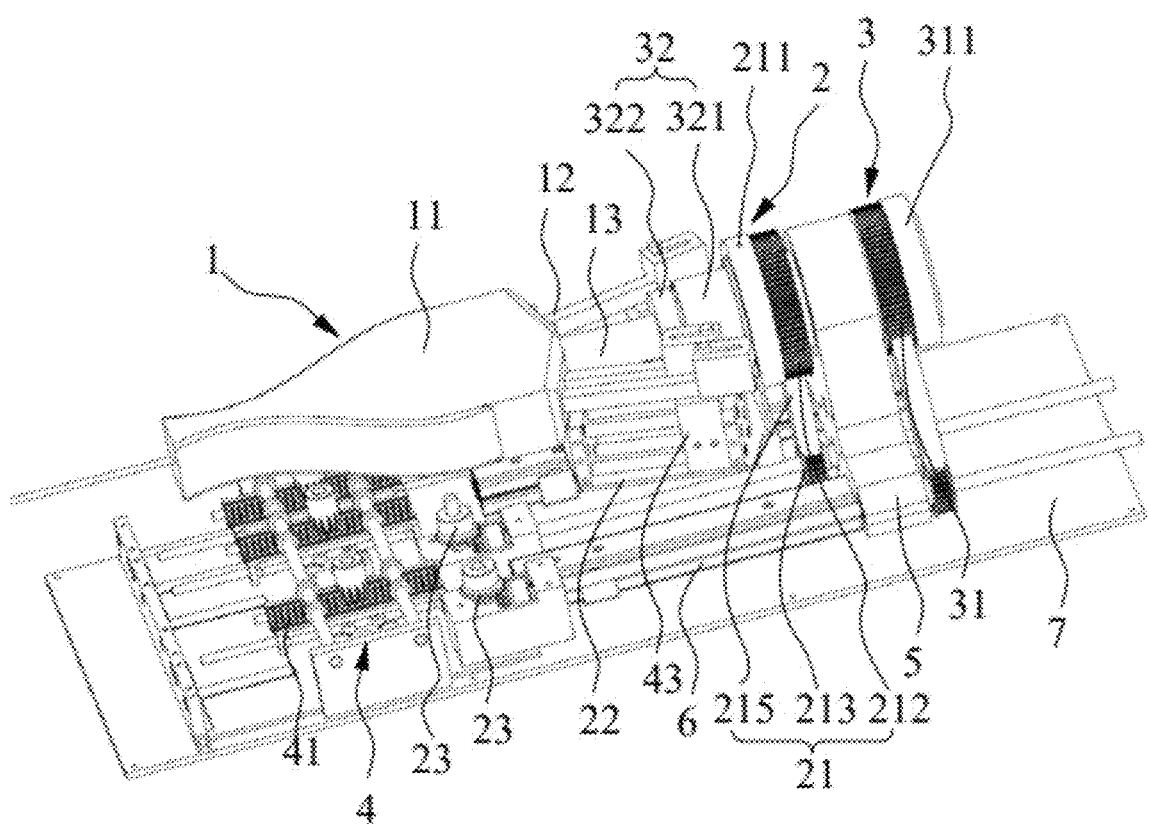
FIG. 1 is a first schematic structural diagram of the instrument drive apparatus according to the embodiments of the present disclosure, with the flexible push-pull wires being not shown.
Figure 2:
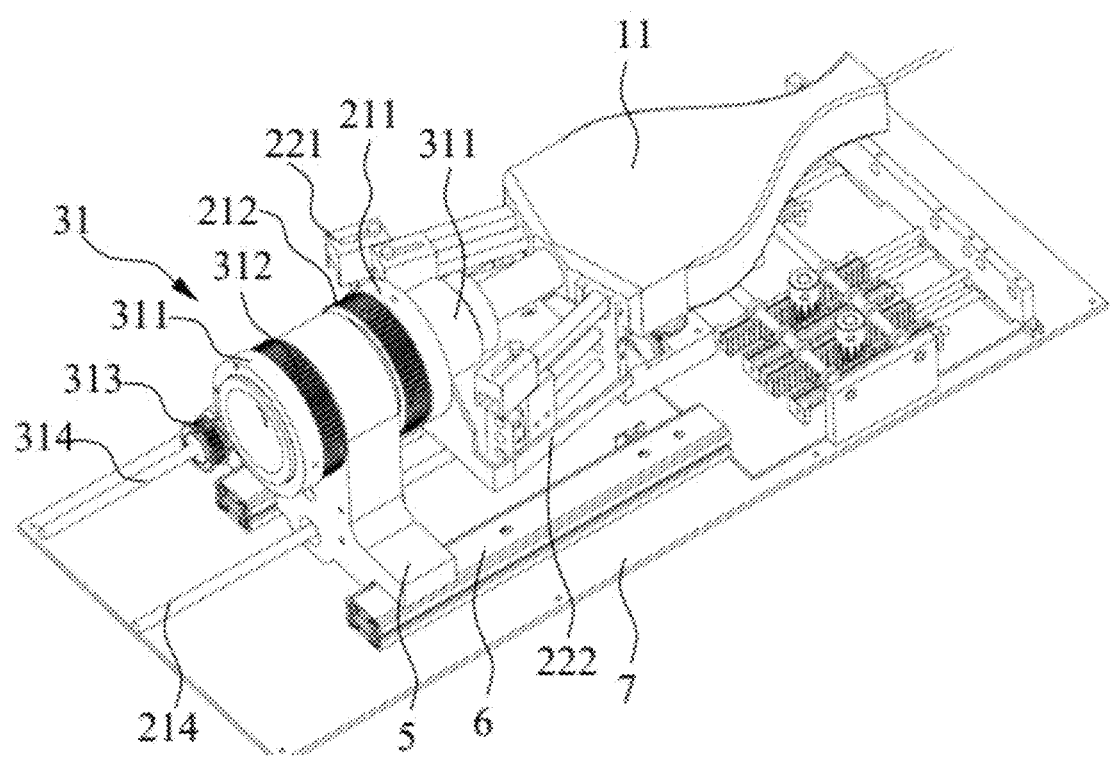
FIG. 2 is a second schematic structural diagram of the instrument drive apparatus according to the embodiments of the present disclosure, with the flexible push-pull wires being not shown.
Figure 3:
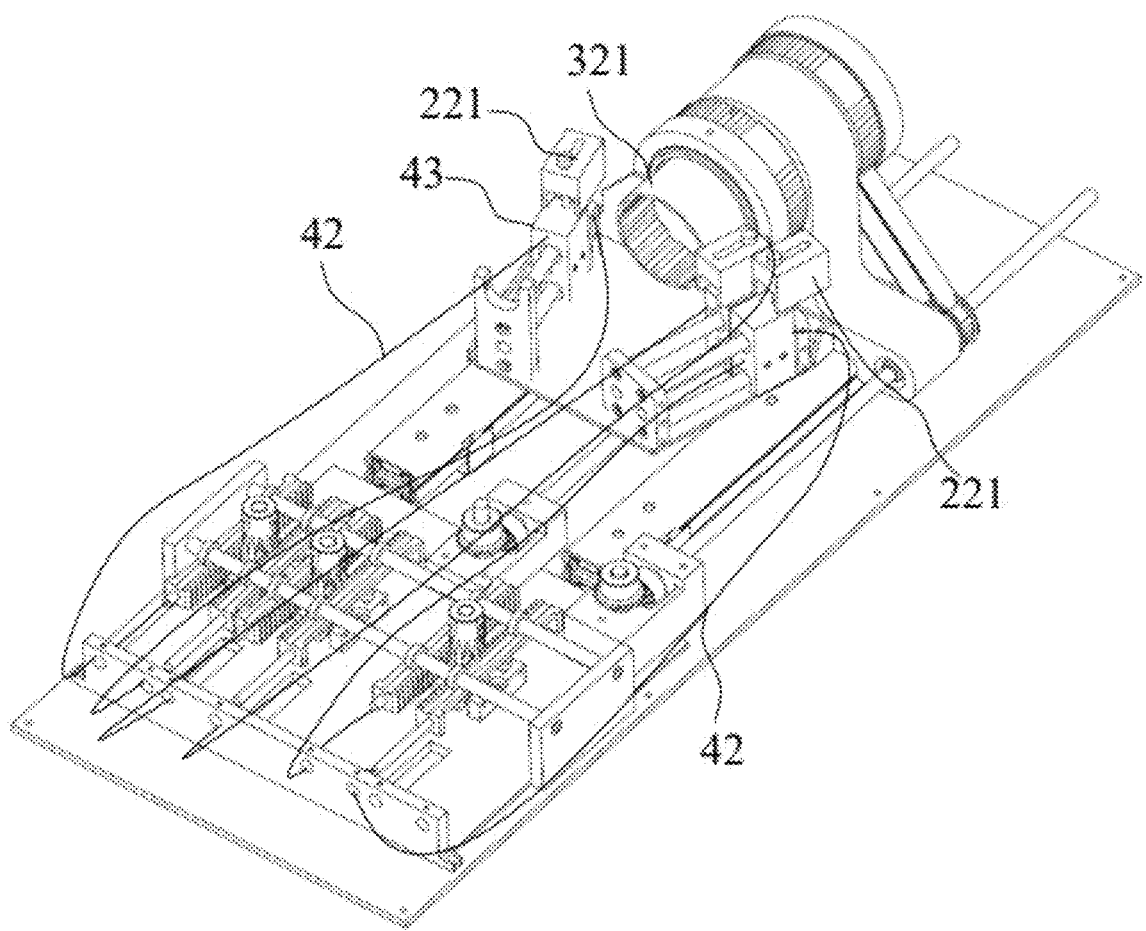
FIG. 3 is a partial structural schematic diagram of the instrument drive apparatus according to the embodiments of the present disclosure.

In the drawings:
- 1: Instrument assembly; 11: Handle; 12: Operating lever; 13: Rotary rod; 2: First rotary drive assembly; 21: First rotary drive mechanism; 211: Rotary seat driving wheel; 212: First transmission wheel; 213: First transmission gear; 214: First transmission shaft; 215: First belt; 22: Rotary seat mechanism; 221: Clamping member; 2211: Clamping seat; 2212: Tightening screw; 222: Base; 23: Bevel gear set; 3: Second rotary drive assembly; 31: Second rotary drive mechanism; 311: Knob driving wheel; 312: Second transmission wheel; 313: Second transmission gear; 314: Second transmission shaft; 315: Second belt; 32: Rotary wheel mechanism; 321: Knob sleeve; 322: Inner sheath drive wheel;
- 4: Push-pull drive assembly; 41: Push-pull drive mechanism; 411: Drive gear; 412: First transmission rack; 413: Second transmission rack; 414: Drum; 42: Flexible push-pull wire; 421: First section; 422: Second section; 43: Slider; 44: Tensioning mechanism; 441: Adjustment bracket; 442: Limit bracket; 443: Tensioning sheath; 444: Adjustment bolt; 45: Guide rod; 5: Support tailstock; 6: Linear guide rail; 7: Installation platform.

DETAILED DESCRIPTION

The present disclosure is further described in detail below in conjunction with the accompanying drawings and embodiments. It can be understood that the specific embodiments described herein are only used to explain the present disclosure, not to limit the present disclosure. It should also be noted that, for the convenience of description, only the parts related to the present disclosure are shown in the accompanying drawings, not all structures.

In the description of the present disclosure, unless otherwise explicitly specified and defined, the terms "connect", "couple" and "fix" should be comprehended in a broad sense, and may refer to, for example, fixed or detachable connections, or integrated connections; mechanical or electrical connections; direct connections or indirect connections through intermediate mediums, or communication between interiors of two elements or interaction between two elements. For a person of ordinary skill in the art, the specific meanings of these terms in the present disclosure can be understood based on specific circumstances.

In the present disclosure, unless otherwise explicitly specified and defined, when a first feature is described as being "above" or "below" a second feature, it includes both direct contact between the first and second features and indirect contact through an additional feature therebetween. Moreover, when a first feature is described as being "above", "over" and "on" a second feature, it includes both the case where the first feature is directly above the second feature and the case where the first feature is obliquely above the second feature, or simply indicates that the first feature is at a higher level than the second feature. When the first feature is described as "below", "under" and "beneath" the second feature, it includes both the case where the first feature is directly below the second feature and the case where the first feature is obliquely below the second feature, or simply indicates that the first feature is at a lower level than the second feature.

In the description of this embodiment, the terms such "upper", "lower", "left", "right" indicate the relative positions or orientations based on those as shown in the drawings, for the purpose of concise description of the present disclosure only, rather than indicating or implying that the device or element referred to must have a particular orientation, or be constructed and operated in a particular orientation. Furthermore, the terms such as "first" and "second" are for a distinguishing purpose only, and should not be construed as indicating or implying relative importance.

In the present disclosure, the term "object" generally refers to a component or a group of components. Throughout the specification and claims, the terms "object", "component", "part", "element" and "member" are used interchangeably.

In the present disclosure, the terms "instrument", "surgical instrument" and "surgical device" are used herein to describe a medical device configured to be inserted into a patient's body and used to perform surgical or diagnostic procedures, including end effectors. The end effectors can be surgical tools associated with one or more surgical tasks, such as forceps, needle holders, scissors, bipolar cauterizers, tissue stabilizers or retractors, clip applicators, stapling devices, imaging devices, and the like.

Some instruments used in embodiments of the present application further provide articulated supports for surgical tools so that the end effector can be manipulated in position and orientation relative to the instrument axis with one or more mechanical degrees of freedom. Furthermore, many end effectors include functional mechanical degrees of freedom, such as jaws that open or close or a knife that translates along a path. The instruments may also contain stored information that is permanent or updateable by the surgical system. Accordingly, the system may provide one-way or two-way information communication between the instruments and one or more system components.

In the present disclosure, the term "match" can be broadly understood as any situation in which two or more objects are connected in a manner that allows the matched objects to operate in conjunction with each other. It should be noted that matching does not require direct connection (e.g., direct physical or electrical connection), but multiple objects or components may be used to match two or more objects. For example, objects A and B may be matched by using object C. In addition, the term "removably coupled" or "removably matched" may be interpreted as meaning a non-permanent coupling or matching between two or more objects. This means that the removably coupled objects may be uncoupled and separated so that they no longer operate in conjunction with each other.

In this context, the terms "or" and "and/or" as used herein should be interpreted as inclusive or meaning any one or any combination. Therefore, "A, B, or C" or "A, B, and/or C" means any one of the following: A; B; C; A and B; A and C; B and C; A, B, and C. Exceptions to this definition would only occur if a combination of elements, functions, steps, or operations are inherently mutually exclusive in some way.

As shown in FIGS. 1 to 8, the present embodiments first provide an instrument drive apparatus for controlling an end effector (not showns). The present embodiments do not limit the specific structure of the end effector.

The instrument drive apparatus includes a drive member (such as a motor, not showns), an instrument assembly 1, a first rotation drive assembly 2, a second rotation drive assembly 3 and a push-pull drive assembly 4. The instrument assembly 1 includes a handle 11, at least two operating levers 12, and a rotary rod 13. The operating levers 12 are slidably connected to the handle 11, and the rotary rod 13 is rotatably connected to the handle 11. The end effector can be controlled to perform different operations through the respective movements of the handle 11, the operating levers 12 and the rotary rod 13.

The first rotary drive assembly 2 includes a first rotary drive mechanism 21 and a rotary seat mechanism 22, where the first rotary drive mechanism 21 has an output end connected to the rotary seat mechanism 22 that is connected to the instrument assembly 1 so as to drive the rotation of the instrument assembly 1; the second rotary drive assembly 3 includes a second rotary drive mechanism 31 and a rotary wheel mechanism 32, where the second rotary drive mechanism 31 has an output end connected to the rotary wheel mechanism 32 that is in transmission connection to the rotary rod 13 so as to drive the rotation of the rotary rod 13.

The push-pull drive assembly 4 includes push-pull drive mechanisms 41 and at least two flexible push-pull wires 42, where the flexible push-pull wires 42 are disposed between the operating levers 12 and the output ends of the push-pull drive mechanisms 41. The push-pull drive mechanisms 41 can drive the reciprocations of the flexible push-pull wires 42, thereby causing the operating levers 12 to reciprocate. By utilizing the flexibility of the flexible push-pull wires 42, the motions of the driving parts such as motors are converted into the push-pull movements of the operating levers 12, which simplifies the motion transmission chain, enabling the instrument drive apparatus to be lightweight and miniaturized, thus reducing the manufacturing costs. The instrument drive apparatus does not require manual operation, that is, the push-pull movements of the operating levers 12, the rotation of the rotary rod 13, and the overall rotation of the instrument assembly 1 are all driven by the driving parts, thereby eliminating misoperations due to hand tremors and reducing operator fatigue associated with manual operations, thus improving the motion control accuracy of the end effectors. The push-pull movements of the operating levers 12 and the rotation of the rotary rod 13 are independent of the rotation of the instrument assembly 1, thus multiple operations can be performed either independently or in combination at the same time through the instrument assembly 1, thereby meeting surgical requirements.

In one embodiment, the first rotary drive mechanism 21 includes a rotatable rotary seat driving wheel 211 that is connected to the rotary seat mechanism 22 and drives the rotation of the rotary seat mechanism 22, and the second rotary drive mechanism 31 includes a rotatable knob driving wheel 311 that is connected to the rotary rod 13 and drives the rotation of the rotary rod 13, where the rotary seat driving wheel 211 and the knob driving wheel 311 are coaxially arranged, so that the rotation of the rotary seat mechanism 22 does not interfere with the movement of the rotary rod 13, allowing the instrument assembly 1 to perform a greater variety of operations.

Specifically, the rotary seat driving wheel 211 is detachably connected to the base 222 of the rotary seat mechanism 22 via screws.

In one embodiment, the instrument drive apparatus further includes a support tailstock 5, where the support tailstock 5, the instrument assembly 1, the first rotary drive assembly 2, the second rotary drive assembly 3 and the push-pull drive assembly 4 are all arranged on the mounting platform 7. The rotary seat driving wheel 211 rotatably extends through the support tailstock 5 and is hollow from one end to the other, and the knob driving wheel 311 extends through the rotary seat driving wheel 211 and is disposed coaxially with respect thereto, thereby reducing the required axial space, thus achieving more compact structure for the instrument drive apparatus.

In one embodiment, the first rotary drive mechanism 21 further includes a first transmission wheel 212, and the second rotary drive assembly 3 further includes a second transmission wheel 312, where the first transmission wheel 212 and the second transmission wheel 312 are both rotatably connected to the support tailstock 5 and are coaxially arranged. The first transmission wheel 212 drives the rotation of the rotary seat driving wheel 211, and the second transmission wheel 312 drives the rotation of the knob driving wheel 311, thereby facilitating torque transmission and enabling independent coaxial rotations of the rotary seat driving wheel 211 and the knob driving wheel 311.

In one embodiment, the instrument drive apparatus further includes a linear guide rail 6 extending axially along the handle 11, with the support tailstock 5 being slidably connected to the linear guide rail 6. The knob driving wheel 311 is detachably connected to the rotary rod 13, and the operating lever 12 is detachably connected to the rotary seat mechanism 22. When the knob driving wheel 311 is detached from the rotary rod 13 and the rotary seat mechanism 22 is detached from the operating lever 12, the rotary seat mechanism 22 and the knob driving wheel 311 can be driven by the support tailstock 5 to move away from the instrument assembly 1. Conversely, when the rotary seat mechanism 22 and the knob driving wheel 311 are driven by the support tailstock 5 to move towards the instrument assembly 1, their assembly with the instrument assembly 1 can be achieved. This sliding mechanism simplifies the disassembly and assembly process of the instrument drive apparatus, thus facilitating maintenance and repair.

In one embodiment, the first rotary drive mechanism 21 further includes a first drive member and a first transmission gear 213, where the first transmission gear 213 is in transmission connection to the first transmission wheel 212 to transmit the torque of the first drive member. The first drive member adopts a motor (not shown), and the first transmission gear 213 transmits the torque of the motor to the first transmission wheel 212, so that the output shaft of the motor is allowed to be non-coxial with the first transmission wheel 212, thereby avoiding interference with the coaxial alignment of the first transmission wheel 212 and the second transmission wheel 312. The transmission connection between the first transmission gear 213 and the first transmission wheel 212 may be implemented through various structures. As shown in FIG. 1, the first rotary drive mechanism 21 further includes a first belt 215 fitted around the first transmission gear 213 and the first transmission wheel 212.

Figure 4:
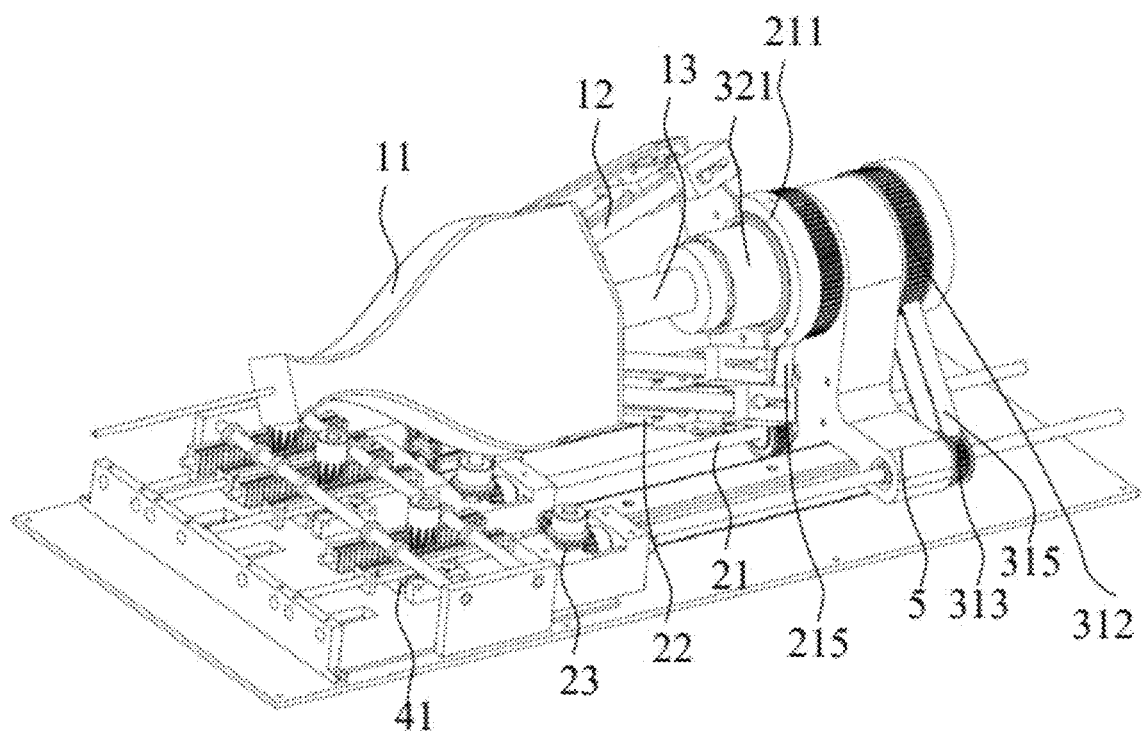
FIG. 4 is a schematic structural diagram of the rotated instrument assembly according to the embodiments of the present disclosure.

In one embodiment, the second rotary drive mechanism 31 further includes a second drive member and a second transmission gear 313, where the second transmission gear 313 is in transmission connection to the second transmission wheel 312 to transmit the torque of the second drive member. The second drive member adopts a motor (not shown), and the second transmission gear 313 transmits the torque of the motor to the second transmission wheel 312, so that the output shaft of the motor is allowed to be non-coaxial with the second transmission wheel 312, thereby avoiding interference with the coaxial alignment of the first transmission wheel 212 and the second transmission wheel 312. Similarly, the transmission connection between the second transmission gear 313 and the second transmission wheel 312 may be implemented through various structures. As shown in FIG. 4, the second rotary drive mechanism 31 further includes a second belt 315 fitted around the second transmission gear 313 and the second transmission wheel 312.

In one embodiment, the first rotary drive mechanism 21 further includes a first transmission shaft 214, and the second rotary drive mechanism 31 further includes a second transmission shaft 314, both being parallel to the linear guide rail 6. The first transmission gear 213 is axially slidably mounted on the first transmission shaft 214 that transmits the torque of the first drive member to the first transmission gear 213, and the second transmission gear 313 is axially slidably mounted on the second transmission shaft 314 that transmits the torque of the second drive member to the second transmission gear 313, so that the first transmission gear 213 can either slide axially on the first transmission shaft 214 or rotate therewith, and the second transmission gear 313 can either slide axially on the second transmission shaft 314 or rotate therewith. The first transmission shaft 214 allows the first drive member and the first transmission gear 213 to be spaced apart from each other, thus facilitating more flexible arrangement according to the spatial layout of the instrument drive apparatus; similarly, the second transmission shaft 314 allows the second drive member and the second transmission gear 313 to be spaced apart from each other, thus facilitating more flexible arrangment according to the spatial layout of the instrument drive apparatus. Moreover, the support tailstock 5 can drive the axial reciprocation of the first transmission gear 213 and the second transmission gear 313, which allows the first transmission gear 213 and the second transmission gear 313 to be pre-assembled with the support tailstock 5 into a single module, enabling detachable connection with the instrument assembly 1 through the movement of the support tailstock 5, thus simplifying the assembly process.

Optionally, the first drive member and the first transmission shaft 214 may be in transmission connection through a pair of bevel gears 23, allowing the output shaft of the first drive member to be arranged perpendicularly to the first transmission shaft 214; similarly, the second drive member and the second transmission shaft 314 may also be in transmission connection through a pair of bevel gears 23, allowing the output shaft of the second drive member to be arranged perpendicularly to the second transmission shaft 314, thereby meeting various spatial requirements and reducing the axial length along the first transmission shaft 214.

In one embodiment, the push-pull drive assembly 4 further includes sliders 43 each slidably connected to the base 222 of the rotary seat mechanism 22. The sliders 43 are fixedly connected to the flexible push-pull wires 42 respectively to be pushed or pulled by the flexible push-pull wires 42 to reciprocate axially along respective operating levers 12. There may be various ways to connect the flexible push-pull wires 42 and the sliders 43, one of which is that a through hole is provided in a slider 43 to extend axially along the operating lever 12 with a flexible push-pull wire 42 passing through the through hole and being fixedly connected to the slider 43, thereby preventing the flexible push-pull wire 42 from being separated from the slider 43, so that the slider 43 can be pulled at one end of the flexible push-pull wire 42 along the through hole to cause the operating lever 12 to slide forward, and the slider 43 can be pulled at the other end of the flexible push-pull wire 42 along the through hole to cause the operating lever 12 to slide backward. Alternatively, the flexible push-pull wire 42 is implemented as two parallel flexible wires which respectively connect to the two opposite ends of the slider 43, allowing the two flexible wires respectively to pull the slider 43 in two opposite directions, thereby enabling the operating lever 12 to slide forward or backward.

Optionally, the rotary seat mechanism 22 includes clamping members 221 detachably connected to the operating levers 12, where the sliders 43 are connected to the clamping members 221 respectively, allowing the sliders 43 to drive the movements of respective clamping members 221, thereby enabling the reciprocations of the operating levers 12.

In order to maintain the stability of the movement directions of the sliders 43, the push-pull drive assembly 4 further includes a plurality of guide rods 45 that are parallel to the linear guide rail 6, where the sliders 43 are slidably mounted on the guide rods 45, avoiding deviations in their sliding directions, thus maintaining the motion control accuracy of the flexible push-pull wires 42.

Figure 5:
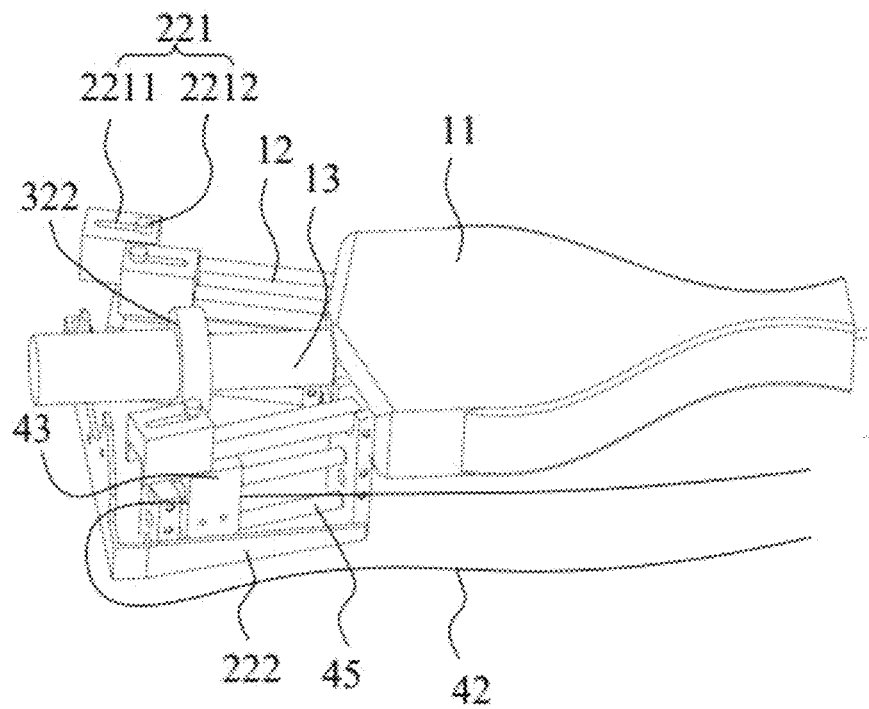
FIG. 5 is a schematic structural diagram of the flexible push-pull wire pushing/pulling the slider according to the embodiments of the present disclosure.

Specifically, each clamping member 221 includes a clamping seat 2211 and a tightening screw 2212, as shown in FIG. 5, where the operating lever 12 is insertably connected to the clamping seat 2211 and secured by the tightening screw 2212, thereby allowing detachable connection between the operating lever 12 and the clamping member 221, thus facilitating the disassembly and assembly.

In one embodiment, the rotary wheel mechanism 32 further includes an inner sheath drive wheel 322 and a knob sleeve 321, the inner sheath drive wheel 322 being connected to one end of the rotary rod 13 that is distal from the handle 11, and the knob sleeve 321 being in transmission connection to the knob driving wheel 311, where the inner sheath drive wheel 322 has external meshing teeth, and the knob sleeve 321 has an inner wall provided with internal meshing teeth, the external meshing teeth and the internal meshing teeth being meshed with each other so that the knob sleeve 321 drives the rotation of the rotary rod 13. When the support tailstock 5 drives the knob sleeve 321 and drives, through the rotary seat mechanism 22, the clamping members 221 so that they move along the linear guide rail 6 to approach the instrument assembly 1 in place, the operating levers 12 are inserted into the clamping seats 2211 for connection thereto and the inner sheath drive wheel 322 is inserted into the knob sleeve 321 for connection thereto, thereby facilitating the connection between the instrument assembly 1 and the first rotating drive assembly 2, the second rotary drive assembly 3, and the push-pull drive assembly 4.

Figure 6:
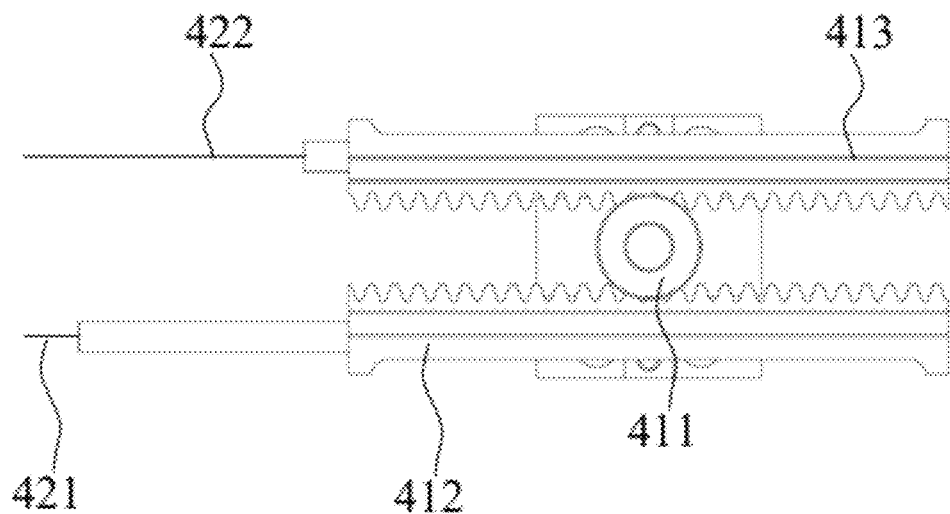
FIG. 6 is a schematic structural diagram of the push-pull drive mechanism driving the flexible push-pull wire according to the embodiments of the present disclosure.

In one embodiment, in order to drive the slider 43 using the flexible push-pull wire 42, as shown in FIG. 6, the push-pull drive mechanism 41 includes a drive gear 411, a first transmission rack 412, and a second transmission rack 413. The first transmission rack 412 and the second transmission rack 413 are meshed with the drive gear 411 at opposite sides and arranged parallel to each other. When the drive gear 411 rotates, the first transmission rack 412 and the second transmission rack 413 can be driven to move in opposite directions at the same time. The flexible push-pull wire 42 includes a first section 421 and a second section 422, where the first section 421 are connected between the first transmission rack 412 and one end of the slider 43, and the second section 422 are connected between the second transmission rack 413 and the other end of the slider 43, thereby allowing either the first section 421 or the second section 422 to pull the slider 43. When the drive gear 411 rotates clockwise as shown in FIG. 6, the first transmission rack 412 moves away from the slider 43 while the second transmission rack 413 moves towards the slider 43, so that the first section 421 pulls the slider 43 to cause the operating lever 12 to move away from the handle 11; correspondingly, when the drive gear 411 rotates counterclockwise as shown in FIG. 6, the first transmission rack 412 moves towards the slider 43 and the second transmission rack 413 moves away from the slider 43, so that the second section 422 pulls the slider 43 to cause the operating lever 12 to move towards the handle 11. It can be understood that due to the flexibility of the flexible push-pull wire 42, the "thrust" applied to the slider 43 is actually achieved by a reverse pulling force.

It should be noted that controlling the movement direction of the slider 43 based on the rotation direction of the drive gear 411 is merely an example. When the first section 421 and the second section 422 of the flexible push-pull wire 42 are connected to the first transmission rack 412, the second transmission rack 413 and the slider 43 at different positions, movement direction control methods therefor vary, which will not be described in detail in this embodiment.

Figure 7:
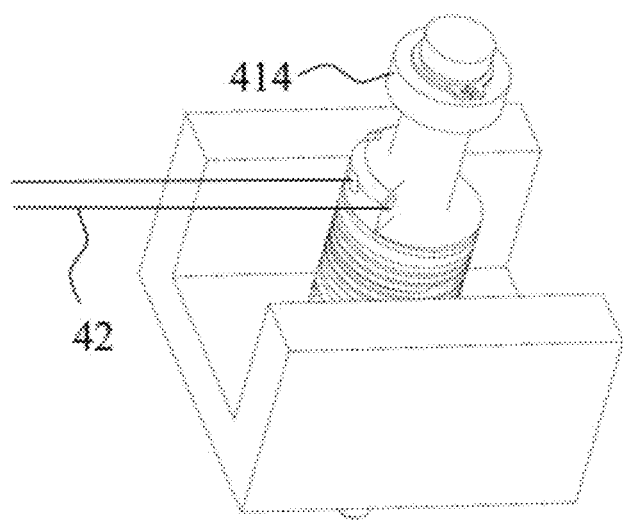
FIG. 7 is a schematic structural diagram of the flexible push-pull wire driven by the drum according to the embodiments of the present disclosure.
Figure 8:
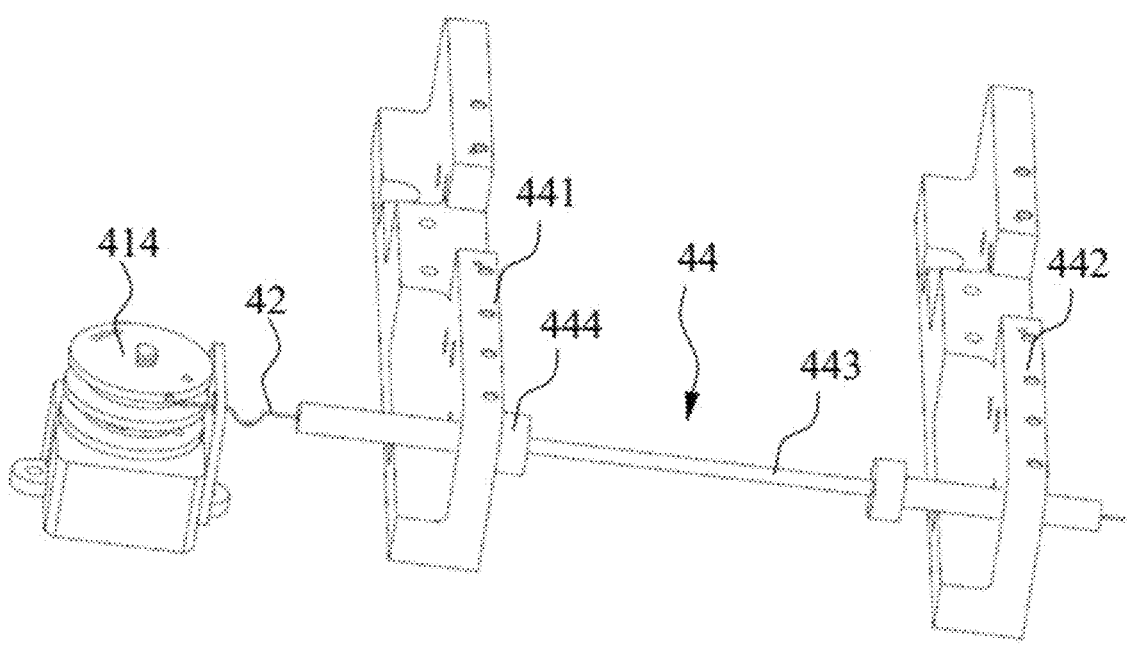
FIG. 8 is a schematic structural diagram of the tensioning mechanism according to the embodiments of the present disclosure.

In one embodiment, the push-pull drive mechanism 41 includes a rotatable drum 414, with the flexible push-pull wire 42 being wound around it, where the flexible push-pull wire 42 having a first end connected to one end of the slider 43, and the second end connected to the other end of the slider 43. Rotation of the drum 414 causes the first end to pull the slider 43, or rotation of the drum 414 in the opposite direction causes the second end to pull the slider 43 in the opposite direction, thereby driving the movement of the operating lever 12 towards or away from the handle 11. The flexible push-pull wire 42 can be wound around the drum 414 for multiple turns, as shown in FIG. 7, where the drum 414 can rotate for multiple turns, thereby achieving a larger stroke of the flexible push-pull wire 42, which is suitable for applications where a larger stroke is required for the operating lever 12. Alternatively, the flexible push-pull wire 42 is wound around the drum 414 for only half a turn, as shown in FIG. 8, where the drum 414 can rotate for no more than one turn, which is suitable for applications where a smaller stroke is required for the operating lever 12, thereby facilitating miniaturization and weight reduction, eliminating the need for an excessively long flexible push-pull wire 42, and enhancing the responsiveness of the flexible push-pull wire 42.

It should be noted that the push-pull drive mechanism 41 further includes a push-pull drive motor (not shown) for controlling the rotation of the drive gear 411 or the drum 414.

In one embodiment, the push-pull drive assembly 4 further includes a tensioning mechanism 44 for tensioning the flexible push-pull wire 42 to prevent the flexible push-pull wire 42 from slipping off the drum 414.

Specifically, the tensioning mechanism 44 includes an adjustment bracket 441, a limit bracket 442, a tensioning sheath 443 and an adjustment bolt 444. The adjustment bracket 441 and the limit bracket 442 are spaced apart from each other and disposed between the drum 414 and the slider 43, with a threaded adjustment hole being provided on the adjustment bracket 441. The tensioning sheath 443 is disposed between the adjustment bracket 441 and the limit bracket 442, and has one end that abuts against the limit bracket 442. The tensioning sheath 443 is made of a flexible material such as a rubber sheath. The flexible push-pull wire 42 extends through the tensioning sheath 443 and is slidable with respect thereto. When the drum 414 rotates to drive the movement of the flexible push-pull wire 42, the tensioning sheath 443 does not move along with the flexible push-pull wire 42. The adjustment bolt 444 is threadedly connected to the threaded adjustment hole, and abuts against an end of the tensioning sheath 443 that is distal from the limit bracket 442, thereby limiting the tensioning sheath 443 between the adjustment bolt 444 and the limit bracket 442.

When the adjustment bolt 444 is rotated on the adjustment bracket 441, the adjustment bolt 444 can push against one end of the tensioning sheath 443, so that the tensioning sheath 443 is bent between the adjustment bolt 444 and the limit bracket 442, resulting in friction between the bent tensioning sheath 443 and the flexible push-pull wire 42, thereby driving the movement of the flexible push-pull wire 42 toward the limit bracket 442, thus tightening the loose flexible push-pull wire 42 between the adjustment bracket 441 and the drum 414.

It should be noted that the specific structure of the tensioning mechanism 44 described above is provided as an example and is not intended to be limiting.

The embodiment of the present disclosure also provides a surgical system including the aforementioned instrument drive apparatus. The surgical system further includes an end effector connected to the instrument drive apparatus, where the handle 11 and/or the operating levers 12 and/or the rotary rod 13 of the instrument drive apparatus are used to drive the movement of the end effector. The motions of the driving parts such as motors are converted into the push-pull movements of the operating levers 12 by utilizing the flexibility of the flexible push-pull wires 42, thereby simplifying the motion transmission chain, which in turn enables the instrument drive apparatus to be lightweight and miniaturized and thus reduces the manufacturing costs. Moreover, the instrument drive apparatus does not require manual operation, that is, the push-pull movements of the operating levers 12, the rotation of the rotary rod 13 and the overall rotation of the instrument assembly 1 are all driven by the driving parts, thereby eliminating misoperations due to hand tremors and reducing the operator fatigue associated with the manual operations, thus improving the motion control accuracy of the end effector. As a result, the surgical system achieves high precision and reliability.

It is evident that the described embodiments of the present disclosure are merely illustrative examples provided to elucidate the present disclosure, and do not constitute limitations on the implementation of the present disclosure. A person of ordinary skill in the art can make various changes or modifications on the basis of the above description. It is neither necessary nor possible to exhaustively enumerate all possible implementations. Any modifications, equivalent substitutions, and improvements made within the spirit and principle of the disclosure are intended to be encompassed within the scope of the appended claims.

What is claimed is:

1. An instrument drive apparatus, comprising:
    an instrument assembly (1) comprising a handle (11), at least two operating levers (12), and a rotary rod (13), the operating levers (12) being slidably connected to the handle (11), and the rotary rod (13) being rotatably connected to the handle (11);
    a first rotary drive assembly (2) comprising a first rotary drive mechanism (21) and a rotary seat mechanism (22), the rotary seat mechanism (22) being connected to the instrument assembly (1), and the first rotary drive mechanism (21) having an output end connected to the rotary seat mechanism (22);
    a second rotary drive assembly (3) comprising a second rotary drive mechanism (31) and a rotary wheel mechanism (32), the rotary wheel mechanism (32) being in transmission connection to the rotary rod (13), and the second rotary drive mechanism (31) having an output end connected to the rotary wheel mechanism (32); and
    a push-pull drive assembly (4) comprising push-pull drive mechanisms (41) and at least two flexible push-pull wires (42), the flexible push-pull wires (42) being disposed between the operating levers (12) and output ends of the push-pull drive mechanisms (41) respectively.

2. The instrument drive apparatus according to claim 1, wherein the push-pull drive assembly (4) further comprises sliders (43) respectively connected to the operating levers (12); each of the push-pull drive mechanisms (41) comprises a drive gear (411), a first transmission rack (412) and a second transmission rack (413), the first transmission rack (412) and the second transmission rack (413) being meshed with the drive gear (411) at opposite sides and arranged parallel to each other; and each of the flexible push-pull wires (42) comprises a first section (421) and a second section (422), the first section (421) being connected between the first transmission rack (412) and one end of a corresponding one of the sliders (43), and the second section (422) being connected between the second transmission rack (413) and the other end of the corresponding one of the sliders (43).

3. The instrument drive apparatus according to claim 2, wherein the first rotary drive mechanism (21) comprises a rotatable rotary seat driving wheel (211) connected to the rotary seat mechanism (22), and the second rotary drive mechanism (31) comprises a rotatable knob driving wheel (311) connected to the rotary rod (13), the rotary seat driving wheel (211) and the knob driving wheel (311) being coaxially arranged.

4. The instrument drive apparatus according to claim 1, wherein the push-pull drive assembly (4) further comprises sliders (43) respectively connected to the operating levers (12), and the push-pull drive mechanisms (41) comprise rotatable drums (414) respectively, the flexible push-pull wires (42) being wound around the drums (414) respectively, with each of the flexible push-pull wires (42) having a first end connected to one end of a corresponding one of the sliders (43) and a second end connected to the other end of the corresponding one of the sliders (43).

5. The instrument drive apparatus according to claim 3, wherein the push-pull drive assembly (4) further comprises a tensioning mechanism (44) comprising:
- an adjustment bracket (441) and a limit bracket (442) spaced apart from each other and arranged sequentially between the drums (414) and the sliders (43), the adjustment bracket (441) being provided with a threaded adjustment hole;
- a tensioning sheath (443) disposed between the adjustment bracket (441) and the limit bracket (442) and having one end that abuts against the limit bracket (442), wherein a corresponding one of the flexible push-pull wires (42) extends through the tensioning sheath (443) and is slidable with respect thereto; and
- an adjustment bolt (444) threadedly connected to the threaded adjustment hole and abutting against an end of the tensioning sheath (443) that is distal from the limit bracket (442), so that one end of the tensioning sheath (443) can be pushed by the adjustment bolt (444) to cause the tensioning sheath (443) to bend to tension the corresponding one of the flexible push-pull wires (42).

6. The instrument drive apparatus according to claim 5, wherein the first rotary drive mechanism (21) comprises a rotatable rotary seat driving wheel (211) connected to the rotary seat mechanism (22), and the second rotary drive mechanism (31) comprises a rotatable knob driving wheel (311) connected to the rotary rod (13), the rotary seat driving wheel (211) and the knob driving wheel (311) being coaxially arranged.

7. The instrument drive apparatus according to claim 4, wherein the first rotary drive mechanism (21) comprises a rotatable rotary seat driving wheel (211) connected to the rotary seat mechanism (22), and the second rotary drive mechanism (31) comprises a rotatable knob driving wheel (311) connected to the rotary rod (13), the rotary seat driving wheel (211) and the knob driving wheel (311) being coaxially arranged.

8. The instrument drive apparatus according to claim 1, wherein the first rotary drive mechanism (21) comprises a rotatable rotary seat driving wheel (211) connected to the rotary seat mechanism (22), and the second rotary drive mechanism (31) comprises a rotatable knob driving wheel (311) connected to the rotary rod (13), the rotary seat driving wheel (211) and the knob driving wheel (311) being coaxially arranged.

9. The instrument drive apparatus according to claim 8, further comprising a support tailstock (5), wherein the rotary seat driving wheel (211) rotatably extends through the support tailstock (5) and is hollow from one end to the other, and the knob driving wheel (311) extends through the rotary seat driving wheel (211) and is disposed coaxially with respect thereto.

10. The instrument drive apparatus according to claim 9, wherein the first rotary drive mechanism (21) further comprises a first transmission wheel (212), and the second rotary drive assembly (3) further comprises a second transmission wheel (312), the first transmission wheel (212) and the second transmission wheel (312) being both rotatably connected to the support tailstock (5) and coaxially arranged, the rotary seat driving wheel (211) being driven by the first transmission wheel (212) to rotate, and the knob driving wheel (311) being driven by the second transmission wheel (312) to rotate.

11. The instrument drive apparatus according to claim 10, wherein the first rotary drive mechanism (21) further comprises a first drive member and a first transmission gear (213), the first transmission gear (213) being in transmission connection to the first transmission wheel (212); and/or the second rotary drive mechanism (31) further comprises a second drive member and a second transmission gear (313), the second transmission gear (313) being in transmission connection to the second transmission wheel (312).

12. The instrument drive apparatus according to claim 11, further comprising a linear guide rail (6) extending axially along the handle (11), the support tailstock (5) being slidably connected to the linear guide rail (6), wherein the first rotary drive mechanism (21) further comprises a first transmission shaft (214), and the second rotary drive mechanism (31) further comprises a second transmission shaft (314), the first transmission shaft (214) and the second transmission shaft (314) being both parallel to the linear guide rail (6), the first transmission gear (213) being axially slidably mounted on the first transmission shaft (214), and the second transmission gear (313) being axially slidably mounted on the second transmission shaft (314).

13. The instrument drive apparatus according to claim 12, wherein the push-pull drive assembly (4) further comprises sliders (43) slidably connected to the rotary seat mechanism (22), the rotary seat mechanism (22) comprising clamping members (221) detachably connected to the operating levers (12) respectively, the sliders (43) being connected to the clamping members (221) respectively and fixedly connected to the flexible push-pull wires (42) respectively; and/or, the rotary wheel mechanism (32) further comprises an inner sheath drive wheel (322) and a knob sleeve (321), wherein the inner sheath drive wheel (322) is connected to one end of the rotary rod (13) that is distal from the handle (11), and the knob sleeve (321) is in transmission connection to the knob driving wheel (311), the inner sheath drive wheel (322) having external meshing teeth, and the knob sleeve (321) having an inner wall provided with internal meshing teeth, with the external meshing teeth and the internal meshing teeth being meshed with each other.

14. The instrument drive apparatus according to claim 11, wherein the push-pull drive assembly (4) further comprises sliders (43) slidably connected to the rotary seat mechanism (22), the rotary seat mechanism (22) comprising clamping members (221) detachably connected to the operating levers (12) respectively, the sliders (43) being connected to the clamping members (221) respectively and fixedly connected to the flexible push-pull wires (42) respectively; and/or, the rotary wheel mechanism (32) further comprises an inner sheath drive wheel (322) and a knob sleeve (321), wherein the inner sheath drive wheel (322) is connected to one end of the rotary rod (13) that is distal from the handle (11), and the knob sleeve (321) is in transmission connection to the knob driving wheel (311), the inner sheath drive wheel (322) having external meshing teeth, and the knob sleeve (321) having an inner wall provided with internal meshing teeth, with the external meshing teeth and the internal meshing teeth being meshed with each other.

15. The instrument drive apparatus according to claim 9, further comprising a linear guide rail (6) extending axially along the handle (11), wherein the support tailstock (5) is slidably connected to the linear guide rail (6), the knob driving wheel (311) is detachably connected to the rotary rod (13), and the operating lever (12) is detachably connected to the rotary seat mechanism (22).

16. The instrument drive apparatus according to claim 15, wherein the push-pull drive assembly (4) further comprises sliders (43) slidably connected to the rotary seat mechanism (22), the rotary seat mechanism (22) comprising clamping members (221) detachably connected to the operating levers (12) respectively, the sliders (43) being connected to the clamping members (221) respectively and fixedly connected to the flexible push-pull wires (42) respectively; and/or, the rotary wheel mechanism (32) further comprises an inner sheath drive wheel (322) and a knob sleeve (321), wherein the inner sheath drive wheel (322) is connected to one end of the rotary rod (13) that is distal from the handle (11), and the knob sleeve (321) is in transmission connection to the knob driving wheel (311), the inner sheath drive wheel (322) having external meshing teeth, and the knob sleeve (321) having an inner wall provided with internal meshing teeth, with the external meshing teeth and the internal meshing teeth being meshed with each other.

\* \* \* \* \*